United States Patent
Reid et al.

(10) Patent No.: US 9,533,013 B2
(45) Date of Patent: Jan. 3, 2017

(54) METHOD OF TREATING PANCREATIC AND LIVER CONDITIONS BY ENDOSCOPIC-MEDIATED (OR LAPAROSCOPIC-MEDIATED) TRANSPLANTATION OF STEM CELLS INTO/ONTO BILE DUCT WALLS OF PARTICULAR REGIONS OF THE BILIARY TREE

(71) Applicants: University of North Carolina at Chapel Hill, Chapel Hill, NC (US); Diabetes Research Institute, Miami, FL (US); Sapienza Università di Roma, Rome (IT)

(72) Inventors: Lola M. Reid, Chapel Hill, NC (US); Yunfang Wang, Beijing (CH); David A. Gerber, Chapel Hill, NC (US); Giacomo Lanzoni, Miami Beach, FL (US); Luca Inverardi, Miami Beach, FL (US); Juan Dominguez-Bendala, Miramar, FL (US); Domenico Alvaro, Rome (IT); Vincenzo Cardinale, Rome (IT); Eugenio Gaudio, Rome (IT); Guido Carpino, Rome (IT)

(73) Assignees: University of North Carolina at Chapel Hill, Chapel Hill, NC (US); Sapienza Università Di Roma, Rome (IT); University of Miami—Diabetes Research Institute, Miami, FL (US)

( * ) Notice: Subject to any disclaimer, the term of this patent is extended or adjusted under 35 U.S.C. 154(b) by 113 days.

(21) Appl. No.: 14/207,191

(22) Filed: Mar. 12, 2014

(65) Prior Publication Data
US 2014/0301985 A1 Oct. 9, 2014

Related U.S. Application Data

(60) Provisional application No. 61/780,644, filed on Mar. 13, 2013.

(51) Int. Cl.
*A61K 35/407* (2015.01)
*A61L 27/38* (2006.01)
*A61L 27/54* (2006.01)

(52) U.S. Cl.
CPC .......... *A61K 35/407* (2013.01); *A61L 27/3834* (2013.01); *A61L 27/3886* (2013.01); *A61L 27/54* (2013.01); *A61L 2300/414* (2013.01); *A61L 2430/28* (2013.01)

(58) Field of Classification Search
None
See application file for complete search history.

(56) References Cited

U.S. PATENT DOCUMENTS

| | | |
|---|---|---|
| 7,824,911 B2 | 11/2010 | Kubota et al. |
| 2007/0155009 A1 | 7/2007 | McClelland et al. |
| 2008/0248570 A1 | 10/2008 | Turner et al. |
| 2008/0318316 A1 | 12/2008 | Reid et al. |
| 2011/0135610 A1 | 6/2011 | Reid et al. |
| 2011/0223139 A1 | 9/2011 | Chancellor et al. |
| 2011/0274666 A1 | 11/2011 | Turner et al. |
| 2013/0137176 A1 | 5/2013 | Roach et al. |
| 2015/0265656 A1* | 9/2015 | Shamblott ............ C12N 5/0678 424/93.7 |

OTHER PUBLICATIONS

"Anatomy and physiology of the bile ducts" Canadian Cancer Society http://www.cancer.ca/en/cancer-information/cancer-type/bile-duct/anatomy-and-physiology/?region=sk Retrieved Apr. 7, 2016.*
International Search Report and Written Opinion in Int'l Appln No. PCT/US14/26461, mailed Jun. 26, 2014.
Kubota et al., "Clonogenic hepatoblasts, common precursors for hepatocytic and biliary lineages, are lacking classical major histocompatibility complex class I antigen" Proceedings of the National Academy of Sciences, Oct. 24, 2000. vol. 97, No. 22, pp. 12132-12137.
Wang et al., "Biliary Tree Stem Cells, Precursors to Pancreatic Committed Pregenitors: Evidence for Possible Life-Long Pancreatic Organogenesis," Stem Cells, 2013, vol. 31, No. 9, pp. 1966-1979.
Office Action issued in Vietnamese application No. 1-2015-03676 dated Nov. 25, 2015 with English translation.
International Preliminary Report on Patentability mailed Sep. 24, 2015 in corresponding application No. PCT/US2014/026461.

* cited by examiner

*Primary Examiner* — Allison Fox
(74) *Attorney, Agent, or Firm* — Gilberto M. Villacorta; Natasha Iyer; Foley & Lardner LLP

(57) ABSTRACT

A method of repairing diseased or dysfunctional pancreas or liver is provided. The method involves preparation of a suspension of stem cells and/or progenitor cells such as biliary tree stem cells, hepatic stem cells, pancreatic stem cells or their descendants, committed progenitor cells, from healthy tissue of the patient or of the biliary tree of a non-autologous donor and engrafting the cells into the wall of bile ducts near to the organ to be treated. The graft consists of stem cells or progenitors that are admixed with biomaterials and, optionally, with cytokines and/or native epithelial-mesenchymal cells appropriate for the maturational lineage stage of the cells to be engrafted. The cells are specifically introduced to the hepato-pancreatic common duct of the subject for treatment of pancreatic conditions or to the bile duct wall near to the liver for treatment of liver conditions and allowed to migrate to the pancreas or to the liver and expand and then rebuild part or the entirety of the diseased or dysfunctional organ.

22 Claims, 10 Drawing Sheets

Figure 7

Serum-Free, Hormonally Defined Media (HDM)

- Kubota's Medium (KM) for stem cells and progenitors
  - Low calcium (<0.5 mM)
  - No copper
  - Selenium, zinc
  - Insulin, transferrin/Fe
  - HDL and mixture of free fatty acids bound to purified albumin
  - Nicotinamide
  - Nutrient-rich basal medium
  - Low oxygen (~2%)

Kubota and Reid, 2000

- Hormonally Defined Medium (HDM) for mature cells
  Kubota's Medium supplemented with
  - Higher calcium (~0.6 mM)
  - Copper
  - T3, bFGF, HGF
  - Hepatocyte Fate—EGF, glucagon, galactose, oncostatin M, glucocorticoids
  - Cholangiocyte Fate—VEGF, HGF, glucocorticoids
  - Pancreatic Islet Fate—Cyclopamine, Exendin (no glucocorticoids)
  - Higher oxygen levels (~5%)

Wang et al Hepatology, 2010

METHOD OF TREATING PANCREATIC AND LIVER CONDITIONS BY ENDOSCOPIC-MEDIATED (OR LAPAROSCOPIC-MEDIATED) TRANSPLANTATION OF STEM CELLS INTO/ONTO BILE DUCT WALLS OF PARTICULAR REGIONS OF THE BILIARY TREE

CROSS REFERENCE TO RELATED APPLICATIONS

This application claims the benefit of U.S. Provisional Application No. 61/780,644, filed Mar. 13, 2013, which is herein incorporated by reference it its entirety.

FIELD OF THE INVENTION

The present invention is directed generally to the field of cell-based therapies. More specifically, the invention concerns the cell-based therapies, particularly stem/progenitor cell therapies, for the treatment of pancreatic and liver conditions. The determined stem/progenitor cell populations can be biliary tree stem cells, hepatic stem cells, pancreatic stem cells, committed hepatic or pancreatic progenitors, or mesenchymal stem cells. They might also be derivatives of embryonic stem (ES) cells or induced pluripotent stem (iPS) cells.

BACKGROUND OF THE INVENTION

Regenerative medicine has entered a new phase in which stem cell populations are being transplanted into patients to restore damaged or diseased tissues such as liver and pancreas. Liver diseases, potentially leading to organ failure due to hepatitis viruses, alcohol consumption, diet and metabolic disorders, and other causes, constitute a major medical burden world-wide. Similarly, pancreatic conditions, particularly diabetes, are a leading cause of health problems and death world-wide. Stem/progenitor cell therapies represent possible approaches to address these needs for treatment, and clinical programs are expanding world-wide to explore these novel therapies further. Although many types of precursors are being tested for clinical programs treating liver and pancreas, only certain ones are possible for clinical programs in the near term.

Overview of Stem Cell Biology

The stem cells or their descendants, committed progenitors, are capable of both sustained proliferation and differentiation into specialized cells. The crucial defining distinction of stem cells is their ability to self-renew, i.e., to maintain indefinitely a population with identical properties, through either symmetric or asymmetric cell divisions. Progenitors, by contrast, serve a transitory role in the amplification of a cell population during development or regeneration. When the self-renewal capacity of precursors cannot be rigorously ascertained, investigators sometimes use the terminology "stem/progenitor cells". The term is used also for cell therapies involving the use of both stem cells and/or progenitors.

Stem cells in the first stages of the developing mammalian embryo, along with primordial germ cells at later stages, have the remarkable capacity to give rise to all of the body's cell types, and are therefore termed pluripotent. Embryonic stem (ES) cells remain pluripotent during extensive expansion as established cell lines. The self-renewal potential of ES cells appears virtually unlimited, although the accumulation of spontaneous mutations and chromosomal rearrangements eventually degrades their practical utility. Similarly pluripotent stem cells can be generated through the reprogramming of mature somatic cells by the introduction of small sets of defined genetic factors, and the cells are termed induced pluripotent stem (iPS) cells.

Mesenchymal stem cells or MSCs can be derived from bone marrow, adipose tissue, umbilical cord tissue, Wharton's Jelly and amniotic fluid, grow readily in culture under ordinary culture conditions, can be transplanted by a vascular route or by grafting, and lineage restricted to any mesodermal fate (e.g., bone, cartilage, tendon, muscle). They are able to lineage restrict to endodermal or ectodermal fates but with exceedingly low efficiency, so much so that this feature is not of practical utility with respect to clinical programs. The usefulness of MSCs for clinical programs is proving to be primarily by their production of secreted paracrine signals (matrix and soluble factors) or by immune-modulatory mechanisms, findings that have resulted in their use in clinical programs world-wide to alleviate liver conditions and pancreatic conditions including diabetes.

TABLE 1

Intrahepatic Lineage-dependent Phenotypic Traits in Human Livers

| Maturational Lineage Stages | Early (Stages 1-4; zone 1) | Intermediate (Stages 5-6; zone 2) | Late (Stages 7-10; zone 3) |
| --- | --- | --- | --- |
| Cell sizes | 7-9 μm-stem cells<br>10-12 μm--hepatoblasts<br>12-15 μm-committed progenitors<br>17-18 μm-adult cells | ~20-25 μm | ~25-35 μm |
| Ploidy | Diploid | Diploid and with some tetraploid (depends on age of person) | Tetraploid or higher |
| Proliferation | Hyperplastic growth (DNA synthesis with cytokinesis) | Hyperplastic growth and with some hypertrophic growth (depends on the extent of cytokinesis) | Hypertrophic growth (DNA synthesis with negligible cytokinesis) |
| Representative genes expressed | Stem Cells: NCAM, EpCAM, CD44H (no AFP and little to no albumin), CS-PGs[1,4] | Transferrin, TAT[1], Fully regulatable albumin[2] | P4503A4[1], glutathione-S-transferase[1], HP-PGs[4] |

TABLE 1-continued

Intrahepatic Lineage-dependent Phenotypic Traits in Human Livers

| Maturational Lineage Stages | Early (Stages 1-4; zone 1) | Intermediate (Stages 5-6; zone 2) | Late (Stages 7-10; zone 3) |
|---|---|---|---|
| | Hepatoblasts: ICAM-1[1], EpCAM, AFP[1], CD44H, constitutive albumin[2], P450A7[1], HS-PGs[1,4] Hepatocytes: enzymes in glycogen synthesis[1], CX 28[1], HS-PGs[4], partially regulatable albumin[2] | | Factors associated with apoptosis[1] |

Levels of expression are due to lineage-dependent activation of transcription[1], acquisition of relevant regulatory elements in transcription[2], translational mechanism(s)[3], posttranscriptional modifications (e.g., in Golgi)[4]
AFP, alpha-fetoprotein; CD44, receptor for hyaluronans; CS-PG, chondroitin sulfate proteoglycan; CX, connexins (gap junction proteins); Cyp450, cytochrome P450s; HS-PG, heparan sulfate proteoglycan; ICAM-1, intercellular adhesion molecule-1; NCAM, neural cell adhesion molecule; TAT, tyrosine aminotransferase Determined stem cells, commonly called "adult stem cells", are in fetal and postnatal tissues but are restricted to specific lineages defined by a germ layer (ectoderm, mesoderm, endoderm). Determined stem cells (and their descendants, committed progenitors) replenish mature cells that are lost through normal turnover or injury and disease. Some mature cell types, such as blood cells and those lining the gut or the outer layer of the skin, have a limited lifespan and must be replaced rapidly. Other mature cells, such as cardiomyocytes and certain neurons, can persist for years. The proliferation and differentiation of stem cells must be regulated tightly to ensure life-long maintenance of appropriate numbers of specialized cells and of the stem cell compartment itself, under normal conditions and when cells are replaced because of disease or injury.

This invention provides a method for delivery of any stem cell population, most especially for determined stem cells or their committed progenitors, by targeting their delivery by direct injection or by grafting strategies to the reservoir of stem cell niches giving rise to liver and pancreas. For a discussion of grafting methods and "feeder effects" on stem cell cultures, see U.S. patent application Ser. Nos. 12/213,100 and 13/102,939, the disclosures of which are both incorporated in their entirety herein by reference.

Liver, biliary tree and pancreas are mid-gut endodermal organs central to handling glycogen and lipid metabolism, detoxification of xenobiotics, processing of nutrients for optimal utilization, regulation of energy needs, and synthesis of diverse factors ranging from coagulation proteins to carrier proteins (e.g., AFP, albumin, transferrin). The integrity of the body depends heavily on liver, biliary tree, and pancreatic functions, and failure in any of them, especially the liver, results in rapid death. In recent years it has become apparent that these tissues comprise maturational lineages of cells that are in epithelial-mesenchymal cell partnerships. Each lineage tree begins with an epithelial stem cell (e.g., hepatic stem cell) partnered with a mesenchymal stem cell (e.g., an angioblast).

These give rise to cellular descendants that mature coordinately. The maturational process generates epithelial and mesenchymal cells that change step-wise with respect to their morphology, ploidy, growth potential, biomarkers, gene expression and other phenotypic traits. The functions of the liver and of the pancreas are the net sum of phenotypic properties of all of the cells throughout the entire maturational lineages. In Table 1 we provide a representative example of this by summarizing phenotypic properties of parenchymal cells within the liver and at different maturational lineage stages. It is assumed that there are comparable lineage stages from stem cells or progenitors to mature cells and existing in the pancreas, but these have yet to be defined fully.

The pancreas is located retroperitoneally and provides digestive enzymes to the duodenum and hormones regulating metabolism. The organ is particularly sensitive to mechanical handling and has a propensity to release locally its enzymes leading to autolysis. This tendency has limited the types of surgery that can be done with this organ, including cell therapy for a pancreatic disease or condition. The liver is less sensitive to manual manipulation than the pancreas, but access to it requires abdominal surgery or laparoscopy or access through the biliary tree by endoscopy.

The present invention thus contemplates introducing cells to the liver and to pancreas without physically disturbing or compromising the physical integrity of these organs.

SUMMARY OF THE INVENTION

In one embodiment of the present invention, a method of treating pancreatic or liver dysfunctions or conditions is provided, the method comprising: (a) obtaining a suspension of the stem cells or their descendants, committed progenitor cells, respectively; and (b) introducing the suspension into or onto the walls of the hepato-pancreatic common duct—in the case of pancreas—or the walls of the biliary tree nearer to the liver—in the case of liver, wherein a substantial portion of the cells takes residence in the wall, and wherein the cells mature into functional pancreatic or liver cells and migrate (hypothesized to be by "conveyer belt" mechanisms) to the pancreas or liver, thereby treating the pancreatic or liver dysfunction or condition, respectively. The cells may be biliary tree stem cells or their descendants, committed progenitors, or mesenchymal stem cells for both liver and pancreas or hepatic stem cells or committed progenitors for liver or pancreatic stem cells or their committed progenitors for pancreas. In the future if there is success at controlling ES cells or iPS cells with respect to tumorigenic potential so that they might be used clinically, then they too might be delivered in this way for treatment of liver or pancreas conditions.

The suspension of cells may be preferably combined with one or more biomaterials (e.g., collagens, adhesion molecules, proteoglycans, hyaluronans, other glycosaminoglycan chains, chitosan, alginate, and synthetic, biodegradable and biocompatible polymers, or combinations thereof), growth factors (e.g., R-spondin, fibroblast growth factors (FGFs), hepatocyte growth factor (HGF), epidermal growth factor (EGF), vascular endothelial cell growth factor (VEGF), insulin like growth factor I (IGF-1), insulin-like growth factor II (IGF-2), oncostatin-M, leukemia inhibitory factor (LIF), transferrin, insulin, glucocorticoids, growth hormones, estrogens, androgens, thyroid hormones, pituitary hormones, and combinations thereof), additional cells, or combinations thereof, to form a graft complex.

The additional cells may comprise the epithelial stem cells and their mesenchymal partners. For example, biliary tree stem cells (or hepatic stem cells), angioblasts, and precursors to endothelia and stellate cells or combinations thereof, and may be obtained from a portion of the biliary tree of the subject and that is not diseased or dysfunctional and/or from the biliary tree of a non-autologous donor. According to the method, the graft complex (cells+biomaterials+hormones/growth factors) may be introduced by laparoscopic surgery or by endoscopy via injection, by grafting onto the surface of the bile ducts and with a biodegradable covering around the duct(s), or by a sponge.

In another embodiment of the present invention, a method of repairing the function of the liver or pancreas in a subject having a pancreas in a diseased or dysfunctional condition is provided, comprising: (a) obtaining a suspension of the stem cells and/or committed progenitor cells; and (b) introducing the suspension to the walls of the hepato-pancreatic common duct—in the case of pancreas—or the walls of the bile duct nearer to the liver—in the case of liver, wherein a substantial portion of the cells introduced take up residence in or on at least a portion of the pancreas or liver as mature pancreatic cells or liver, respectively, in vivo.

The method is based on an understanding that stem cell populations within the biliary tree are the precursors contributing to organogenesis of the liver and pancreas. The lineages of cells begin within stem cell niches, peribiliary glands, and progress to mature cells within the organs. Peribiliary glands throughout the biliary tree contain cells that exhibit phenotypic traits constituting evidence of maturational lineages going from stem cell populations deep within the bile duct walls (near the fibromuscular layers) to mature cells near the lumens of the bile ducts and with proximity either to liver or pancreas. These cells have been characterized and show changes in phenotypic traits with proximity to the organ.

The biliary tree is a logical target for transplantation of cells in stem cell therapies. There is a network of stem/progenitors organized in maturational lineages in a radial axis and proximal-to-distal axis within the biliary tree and contributing to organogenesis of liver and pancreas throughout life. The advantages of using the biliary tree as the target site for transplantation are many. The transplantation procedures can be done as outpatient procedures (e.g. endoscopy) or as minor surgical procedures (laparoscopy). The strategy enables the transplantation of stem cells or progenitor cells with minimal (if any) immunogenicity and, thereby, provides the potential of avoiding immunosuppressive drugs for the patients. The procedures involve grafting strategies, already demonstrated to facilitate engraftment into the target organ; instead of the approximately 20% engraftment in the liver now documented by many investigators doing cell transplantation by a vascular route, grafting strategies result in nearly 100% engraftment. This avoids ectopic cell distribution, a serious concern in cell transplantation by a vascular route, and optimizes the use of the donor cells (that is avoiding loss of cells from death or from ectopic cell distribution).

The advantages are especially profound for treatment of the pancreas, since its sensitivity to manual manipulation has obviated any chance of cell therapy directly into the organ. Stem cells transplanted into the portion of the biliary tree near to the pancreas, the hepato-pancreatic common duct, overcomes this major difficulty and enables stem cell therapies for the pancreas to become a reality.

The numbers of such primitive stem cells are remarkably high throughout the biliary tree, with an average of 2-4% of the cells in these PBGs. In addition, the PBGs are in high numbers particularly at the branching points of the biliary tree. Shown are some of those sites where there are high numbers of PBGs (schematically shown with the blue stars). The extramural PBGs contain primarily very primitive stem cells (high levels of pluripotency and stem cell genes; negligible levels of mature cell genes) and are tethered to the surface of the bile ducts by a cord of tissue. The highest number of all of PBGs are found in the hepato-pancreatic common duct near the duodenum, and these contain ~9% of their cells as the very primitive stem cells. Thus, the biliary tree is a veritable "root system" of stem cells for liver and pancreas.

Figure 1:
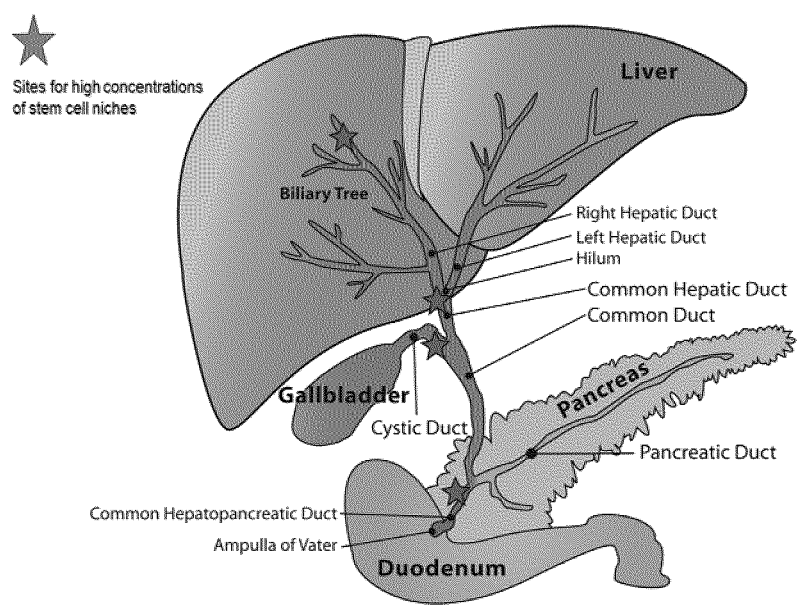
FIG. 1 is a schematic of the liver, biliary tree and pancreas showing their connection to the duodenum. Intramural and extramural peribiliary glands (PBGs), the stem cell niches of the biliary tree, are found throughout the biliary tree. The intramural PBGs are located in high numbers within the walls of the bile ducts, from the most interior sites within the bile ducts, sites near fibromuscular layers, to the sites nearest to the bile duct lumens. The cells within the PBGs near the fibromuscular layers are comprised of the highest numbers of cells that are very primitive (have high levels of pluripotency genes and stem cell genes and minimal, if any, expression of mature cell genes). With transition to the lumens of the bile ducts, (the radial axis of maturation) the pluripotency gene expression fades and the expression of mature cell genes increases.
Figure 2:
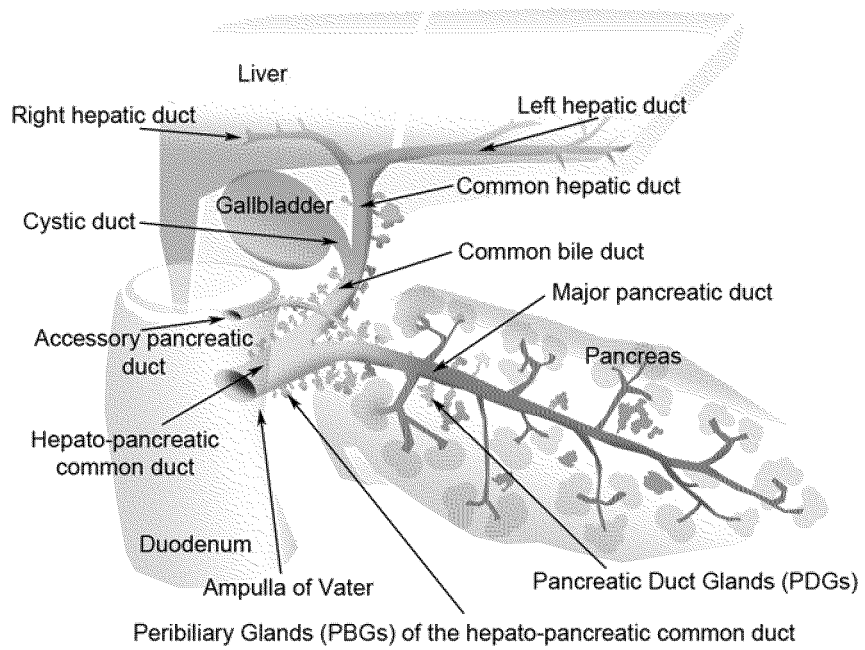

FIG. 2 is a more detailed schematic of the hepato-pancreatic common duct. The formation of the liver and pancreas occurs as an outgrowth of tissue from the duodenum at two sites: that which forms the dorsal pancreatic duct; and that which forms the ventral pancreas duct and the biliary tree leading to the liver. The formation of the intestine results in a twisting motion swinging the ventral pancreatic duct/and common bile duct 180 degrees such that the ventral pancreatic "anlage", the tissue that will give rise to the ventral pancreas, moves to a position beneath that of the dorsal pancreas, and the connecting biliary tree are now located on the left side of the duodenum. The merged hepatic and pancreatic duct are called: "the hepato-pancreatic common duct.

PBGs within the hepato-pancreatic common duct contain biliary tree stem cells that can give rise to either liver and/or pancreas. It is also the site of the highest numbers of pancreatic stem cells, descendants from biliary tree stem cells and with phenotypic traits indicating that they are now determined stem cells for the pancreas. Although there are also a subpopulation of cells qualifying to be hepatic stem cells, the numbers of those increase with progression along the biliary tree to proximities nearer to the liver. It should be noted that even within the liver, in the large intrahepatic bile ducts, there are PBGs that contain a small percentage of cells that are precursors to both liver and pancreas and there are also a small percentage that qualify as pancreatic stem cells and another set qualifying as hepatic stem cells.

Figure 3:
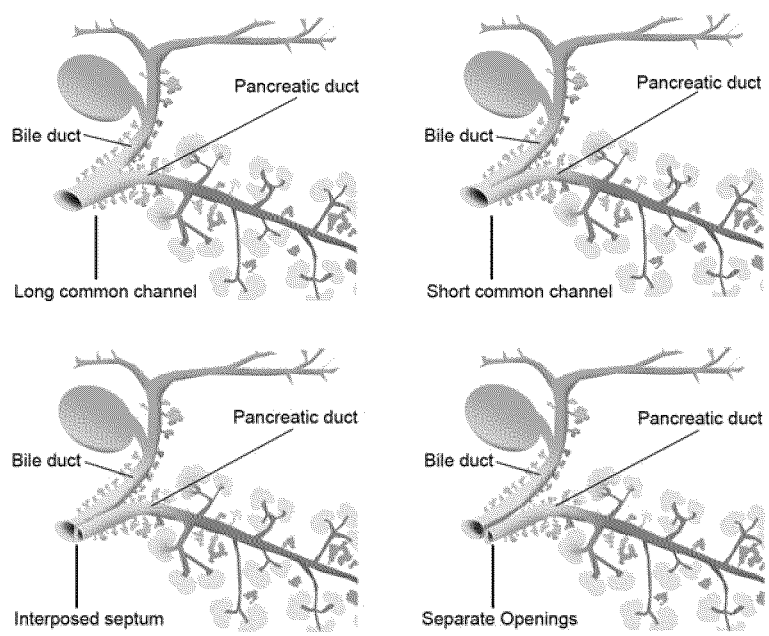

FIG. 3 shows representative variations in the connections of the pancreatic duct and bile duct at the ampulla of Vater. One of the most common variations has an interposed septum. There are variations in humans in how the hepatic and pancreatic ducts merge. This will have a bearing in how transplantation into the hepato-pancreatic common duct might be done. Those in which there is complete fusion of the two (e.g. long and short common channels) will serve as a site for injection/grafting of the cells. Those in which there is an interposed septum between the two or when there are wholly separate channels will be ones requiring transplantation into the relevant one for liver versus pancreas.

Figure 4:
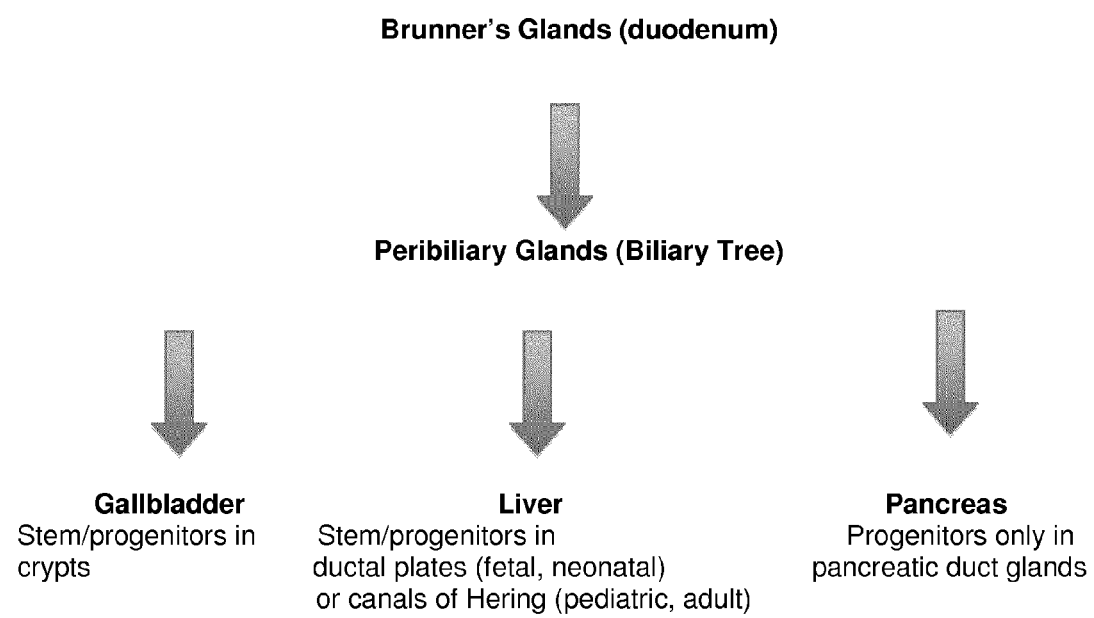

FIG. 4 is a flow chart showing a network of stem cell and progenitor cell niches in the Biliary Tree. The stem cell and progenitor cell niches are found throughout the biliary tree and extending into the liver and into the pancreas. The hypothetical start points of these niches are the Brunner's Glands, found as submucosal glands within the duodenum. These glands are found at no other location within the intestine. Their roles have, in the past, been assumed to be associated with facets of functions of the stomach and duodenum. However, the morphological structure and the phenotypic traits of the cells within the glands overlap extensively with those of the traits of cells within the PBGs.

The PBGS are found throughout the biliary tree. They are found in cystic ducts that lead into the gallbladder. Within the gallbladder, there are no PBGS and here we have found that the stem cells and progenitors are organized differently in that they are localized to crypts (in patterns similar to crypts within the intestine) and give rise to cells that mature with progression to the tops of the villi within the gallbladder.

The PBGs within the liver are in the large intrahepatic bile ducts and these connect anatomically to the ductal plates found in fetal and neonatal livers and that transition to the canals of Hering found in pediatric and adult livers. The PBGs, the ductal plates, and the canals of Hering contain stem cells and progenitors.

The PBGs in the hepato-pancreatic common ducts near the duodenum transition to the pancreatic duct glands within the pancreas. With this transition, the cells convert entirely to committed progenitors. Thus, there are only very rare stem cells within pancreatic ducts or pancreatic duct glands. Rather, the biliary tree stem cells and pancreatic stem cells are localized essentially entirely within the PBGs found in the hepato-pancreatic common duct or in other portions of the biliary tree that are independent of the pancreas.

Figure 5:
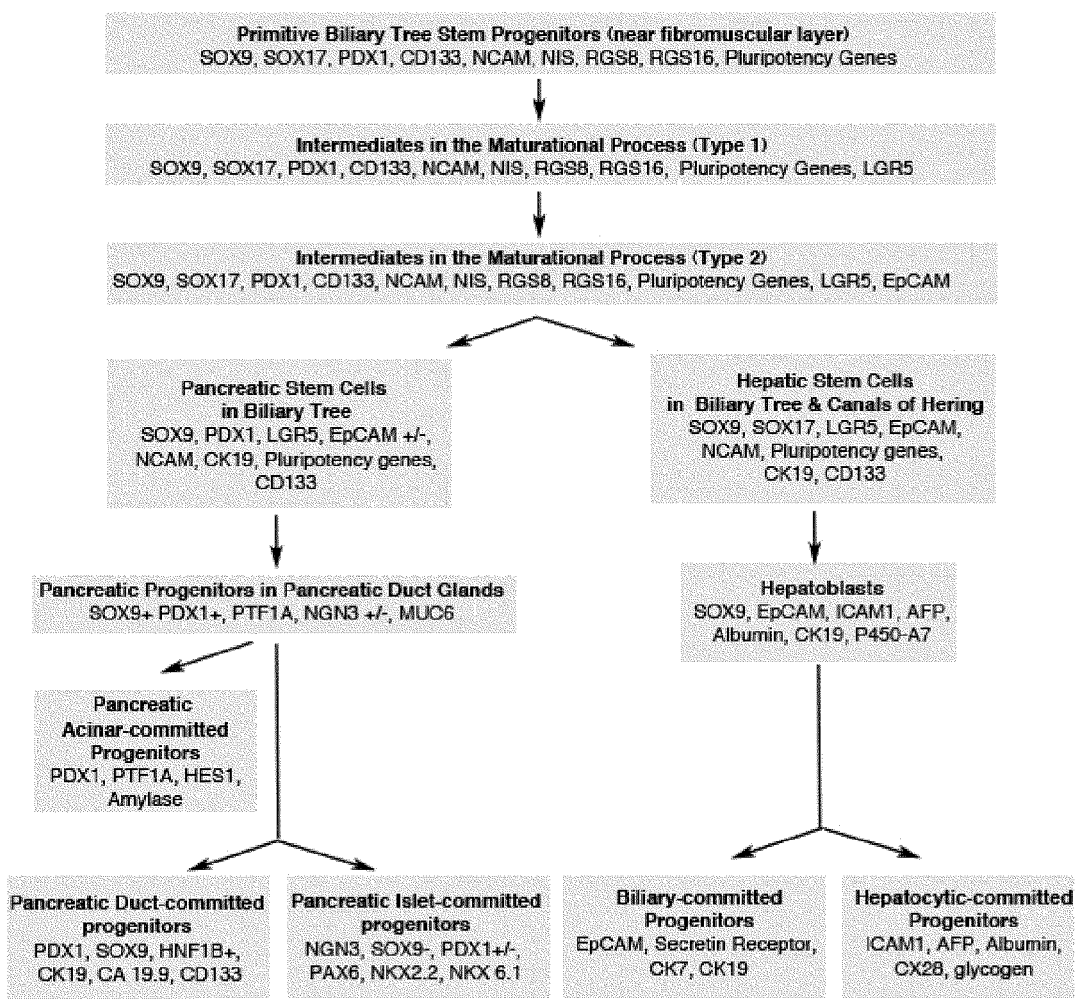

FIG. 5 is a flowchart showing Stem/Progenitor Cell Subpopulations giving rise to Liver, Biliary Tree and Pancreas. There are multiple stem cell and progenitor cell subpopulations throughout the biliary tree. Shown are those in the intramural PBGs and those being the precursors to either liver or pancreas (not shown are those in the gallbladder). Demonstrated are some of the changes in phenotypic traits occurring within the radial axis throughout the biliary tree (the first 3 stages shown). Then shown are those within the hepato-pancreatic common duct with proximity to the pancreas (the lineages of cells descending from the pancreatic stem cells). Alternatively, there are the descendants from the hepatic stem cells found in highest numbers in the PBGs in the large intrahepatic bile ducts and transitioning to the ductal plates (fetal or neonatal) or canals of Hering (pediatric or adult). Phenotypic traits common to all of these lineage stages of stem cells and progenitors are cytokeratin 8 and 18 and sodium iodide symporter (NIS).

Figure 6:
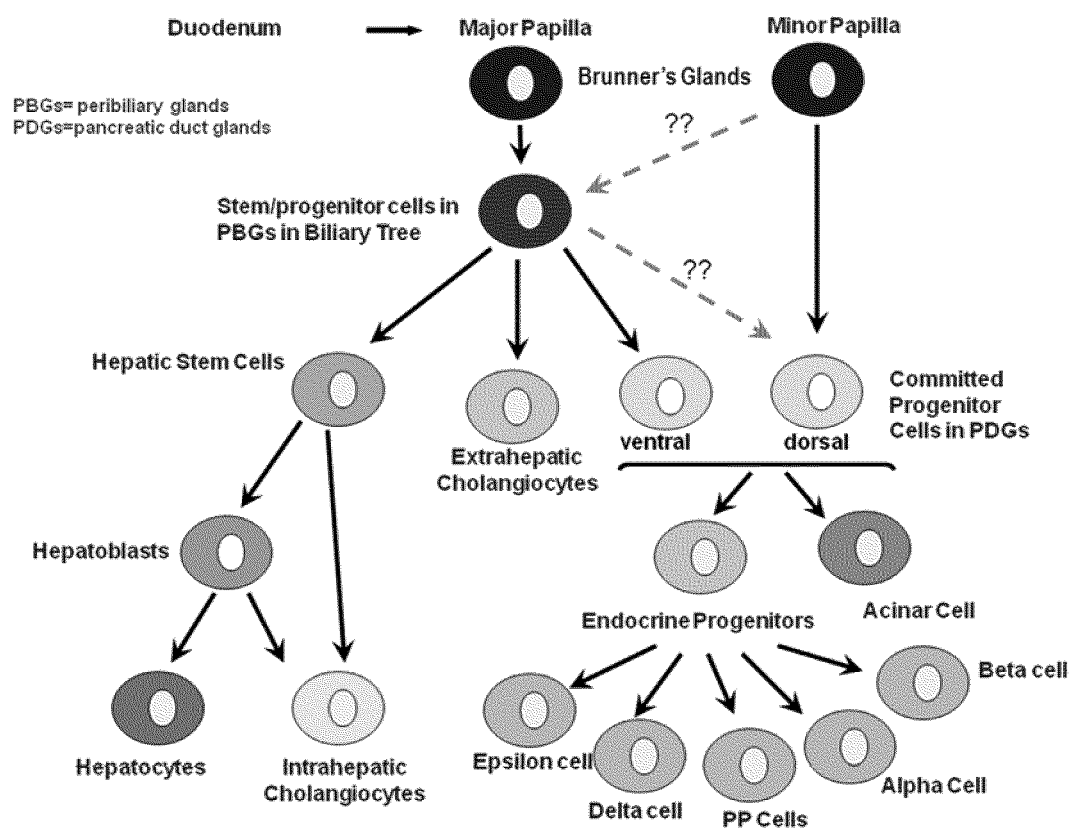

FIG. 6 is a schematic of hypothetical lineages along a proximal-to-distal axis starting from the duodenum and ending with mature cells at either liver or pancreas. The radial axis of lineage stages is complemented by a proximal-to-distal axis of lineage stages. Thus, the highest numbers of very primitive stem cells (high levels of pluripotency gene expression and other stem cell markers) is found in the hepato-pancreatic common duct near to the duodenum. With progression towards the pancreatic ducts, the PBGs increasingly contain higher and higher percentage of cells with markers indicative of a pancreatic fate; once within the pancreatic duct, there are few, if any, traits of stem cells and only traits of committed progenitors and of intermediates in lineages progressing towards acinar or islet cells. With progression along the biliary tree (common duct and then common hepatic duct, etc.) there are increasing percentages of cells within the PBGs with markers indicative of an hepatic fate.

FIG. 7 provides select components of Kubota's Medium and Hormonally Defined Medium. The ability to maintain stem cells and progenitors ex vivo has been dependent on establishment of wholly defined, serum free media comprised of the essential components required by the cells. Kubota's Medium (KM) was established as a serum-free, wholly defined medium for ex vivo maintenance of endodermal stem cells and progenitors. It has proven successful for stem cells and progenitors from liver, biliary tree, pancreas and also from lung and, with some modifications, also for intestine. Kubota's Medium does not permit survival of mature cells, only stem cells and progenitors.

Defined media for the mature cells requires supplementation with additional factors, as noted in the figure, and with specific additions for specific adult fates. These are the soluble factors required for the differentiation process. For optimal achievement of either self-replication for stem cells versus maturation to an adult cell fate requires use of substratum of lineage-stage specific extracellular matrix components. For self-replication, the matrix components include hyaluronans and forms of proteoglycans with minimal sulfation; for maturity to adult cell states require multiple matrix components, ideally those found in biomatrix scaffolds, matrix extracts derived from the adult tissue.

Figure 8:
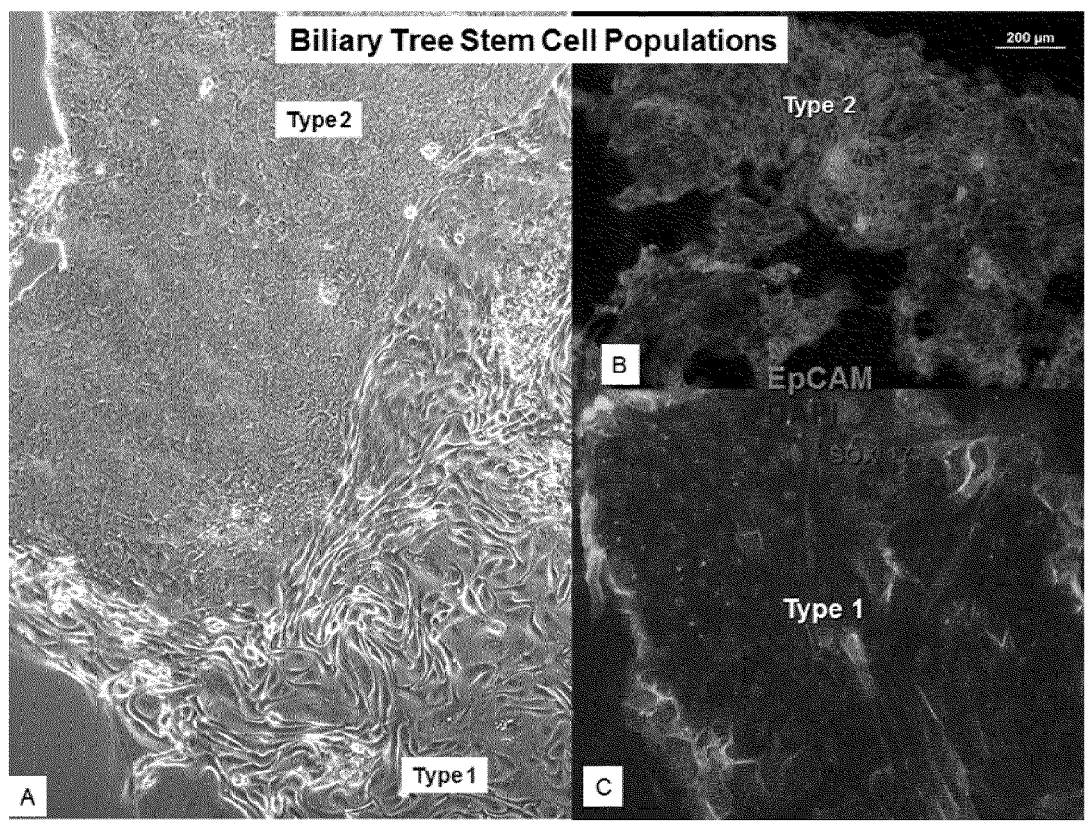

FIG. 8 shows cultures of biliary tree stem cells plated onto plastic and in Kubota's Medium. Under these conditions, there are two major categories of biliary tree stem cells that emerge: type 2 cells express EpCAM on every cells. Type 1 cells do not express EpCAM but acquire expression of it at the edges of colonies, sites at which they are undergoing slight differentiation. Type 1 cells give rise to type 2 cells as shown morphologically in FIG. 8A.

Figure 9:
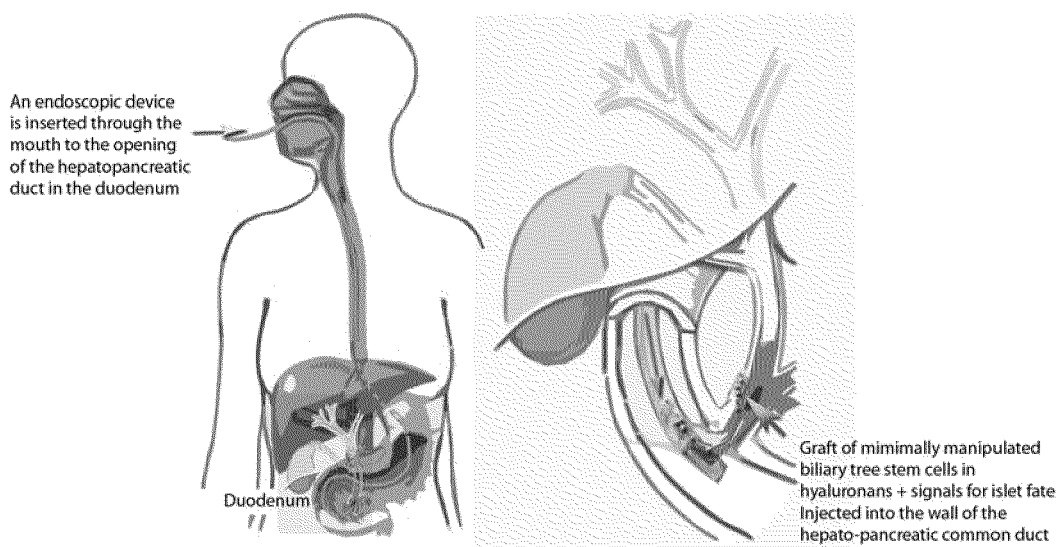

FIG. 9 graphically illustrates the inventive strategy for stem cell therapy of liver or of pancreas using an endoscopic strategy. If the pancreas is being treated, then the graft would be placed within the walls or patched onto the walls of the hepato-pancreatic common duct. If the liver is being treated, then the endoscope would be moved into the common duct and possibly into the common hepatic duct and there grafted into or onto the wall of the duct.

Figure 10:
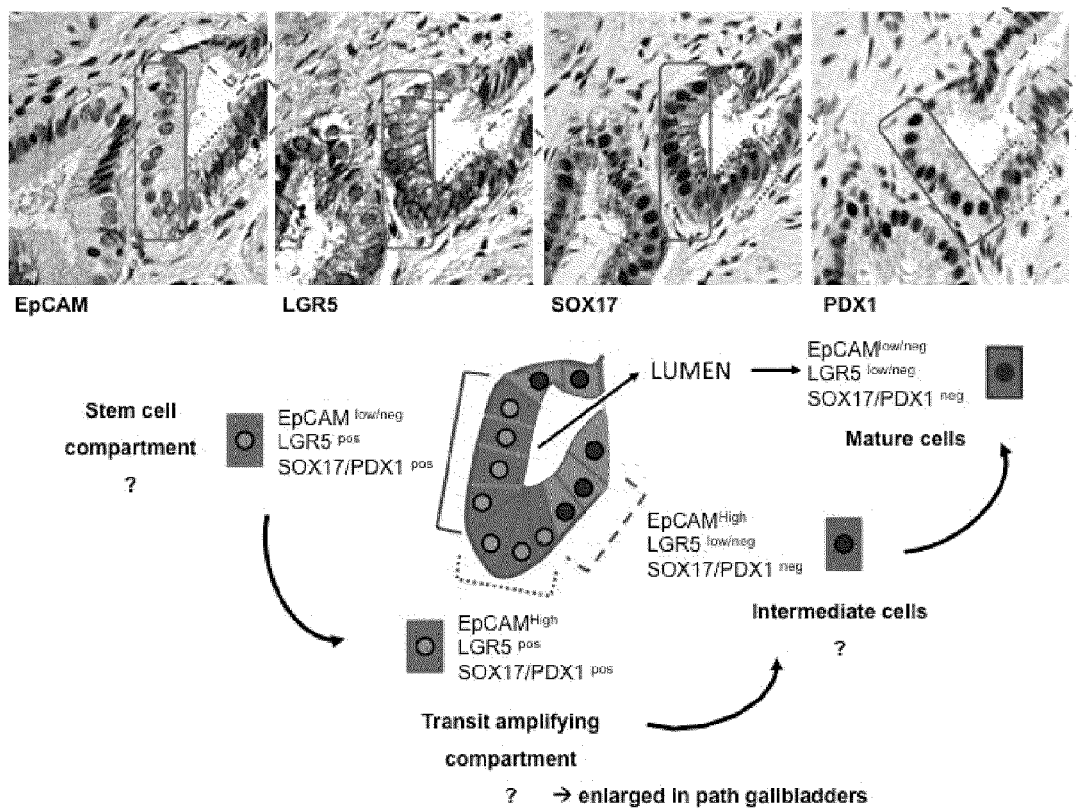

FIG. 10 is immunohistochemistry of human gallbladder demonstrating location of stem cells and progenitors in the crypts.

DETAILED DESCRIPTION OF THE INVENTION

Diabetes is a genetic condition affecting the pancreas and amenable to treatment by cell therapy strategies. (Diabetes is merely a representative of a condition that can be treated by the inventive strategy, but it should be noted, that any liver condition or disease can be treated by a similar process.) The global incidence of diabetes mellitus has increased dramatically over the past few years and continues to rise. The quest for curative therapies that normalize blood glucose levels and provide independence from exogenous insulin therapies impacts patients with type 1 diabetes (T1D) and a significant subset of patients with type 2 diabetes (T2D) who have a functional deficiency in insulin production. Islet transplantation has been attempted, but the approach has been constrained by the limited yield of quality donor pancreata that can be utilized to isolate islets. Therefore, attempts have been made to identify one or more precursor populations that can be lineage restricted to islet cells and, thereby, constitute a nearly limitless and reproducible supply of transplantable and functional islets.

In the past, determined stem cells for pancreas have not been considered an option based on the findings that there are only very rare pancreatic stem cells and instead essentially only committed progenitors in postnatal pancreatic tissue. The committed progenitors in pancreas are found in the pancreatic ducts, particularly in the pancreatic duct glands (PDGs). The phenotype of these committed progenitors and their actual contributions to the endocrine compartment of the pancreas remain actively debated, but it is generally agreed that these are the primary precursor populations for islets and that are found within the pancreas proper.

Recently, a new source of islet precursors was identified in biliary trees in donors of all ages. See U.S. patent application Ser. No. 12/926,161, the disclosure of which is incorporated herein in its entirety by reference. The biliary tree has been found to contain multiple subpopulations of determined stem cells with indefinite expansion potential in culture and that can mature to hepatocytes, cholangiocytes or islets depending on the microenvironment in vitro or in vivo (it is assumed but not yet shown that the stem cells can give rise also to acinar cells).

Peribiliary glands (PBGs) are stem cell niches found within the walls of bile ducts throughout the ramifying biliary tree from the duodenum to the liver and to the pancreas. They occur in high numbers at the branch points of the biliary tree and are especially concentrated in the large intrahepatic bile ducts and in the hepato-pancreatic common duct near the duodenum. The PBGs form direct anatomical connections to reservoirs of stem cells within the liver, the ductal plates of fetal and neonatal livers and that transition to canals of Hering of pediatric and adult livers, and to reservoirs of committed progenitors, the pancreatic duct glands (PDGs), within the pancreas; this network is evident in people of all ages. The network of niches containing stem cells and/or committed progenitors, results in a continuous network of stem cells contributing to the formation of liver, biliary tree, and pancreas supporting an hypothesis of ongoing organogenesis of the liver, biliary tree and pancreas throughout life.

The largest numbers of PBGs, those found in the hepato-pancreatic common duct, connect anatomically to PBGs that transition in their cellular constituents with progression towards liver or to pancreas. Cells within the PBGs morph from homogenous stem cell populations in the hepato-pancreatic common ducts (or the large intrahepatic bile ducts) to ones dominated by progenitors having a particular mature cell fate: mature hepatic parenchymal cells versus mature bile duct cells versus mature pancreas cells, depending on the location of the PBGs within the extrahepatic biliary tree.

The transitions occur along two, overlapping axes: a radial axis and a proximal-to distal axis and with progression occurring hypothetically in a "conveyer belt fashion" analogous to that in the intestine. The radial axis starts with primitive stem cells located in intramural PBGs deep within the bile duct walls at sites near the fibromuscular layer and ending with mature cells at the lumens of the bile ducts. The radial axis near the pancreas shows transitions to pancreatic-like cells; that near the liver transitions to mature hepatic parenchymal cells; those in-between, result in mature cells with bile duct traits.

The proximal-to-distal axis progresses from PBGs containing primitive stem cells next to the duodenum and progresses along the length of the biliary tree to PBGs located within the large intrahepatic bile ducts and thence to canals of Hering within the liver acinus; they contain a mix of stem cells and committed progenitors. The maturational process occurs also from stem cells in PBGs in the hepato-pancreatic common duct near the duodenum to pancreatic duct glands (PDGs) within the pancreas and that contain only committed pancreatic progenitors. The PBGs nearest to the duodenum contain primitive stem cells that express markers of pluripotency (Nanog, OCT4, SOX2, SALL4, KLF4), proliferation (Ki67), and early hepato-pancreatic commitment (SOX17, SOX9, PDX1, LGR5) but do not express intermediate markers such as EpCAM or mature markers such as insulin or albumin. With progression along the maturational axes, there is fading and then loss of pluripotency genes and proliferation markers, maintenance of SOX9 but loss of PDX1 for the progression towards liver, or loss of SOX 17, for the progression towards pancreas. EpCAM is activated in cells at intermediate stages of the maturation and going either to liver, bile duct, or pancreas. Intermediate markers going towards liver include albumin and alpha-fetoprotein (AFP), whereas the ones going towards pancreas include NGN 3, MUC 6 and insulin. See FIG. 5.

The biliary tree stem cells can be isolated by immunoselection or by culture selection. The markers identified to date and by which immunoselection might be done for subpopulations of the biliary tree stem cells from cell suspensions of the biliary tree include epithelial cell adhesion molecule (EpCAM), LGR5, NCAM, CD44 (hyaluronan receptor), and CXCR4. For culture selection, the biliary tree tissue is prepared as a cell suspension and then plated onto culture plastic and in serum-free Kubota's Medium. The details of these protocols are given below.

Under expansion conditions, human biliary-tree-derived stem cells (hBTSCs) are able to proliferate for months as undifferentiated cells, whereas precursors derived from pancreas behave as committed progenitors and undergo only approximately 8-10 divisions but then go through partial endocrine differentiation. A hormonally defined medium (HDM) tailored for differentiation of the cells to islets used in combination with embedding the cells into mixtures of matrix components found associated with islets in vivo results in cell aggregates, spheroids, with ultrastructural, electrophysiological and functional characteristics of neoislets. These neoislets have been able to rescue animals with a diabetic condition by enabling them to produce insulin. Therefore, peribiliary gland-derived stem cells transition to pancreatic duct gland's committed progenitors as part of ongoing pancreatic organogenesis throughout life.

The present invention is predicated on an understanding that treatments of pancreas, including forms of cell therapy, can be targeted to the hepato-pancreatic common duct and these treatments would modify or regulate cells that give rise to the pancreas. The treatments could be delivered to the hepato-pancreatic common duct either by laparoscopic surgery or by endoscopy or by placing the graft as a hydrogel around the outside of the duct along with a covering forming a cuff around the duct and that is surgically glued to the duct. Once delivered, the cells "mature" and migrate, in a conveyer belt fashion, to the pancreas, where they perform "pancreatic" functions, replacing or complimenting the diseased or dysfunctional pancreas. In this way, the pancreas per se is not disturbed in introducing the cells. Rather, the necessary cells are introduced "upstream" and allowed to migrate to their native location within the pancreas.

The present invention is directed to grafting technologies that involve the delivery of transplanted cells as an aggregate on or in scaffolds that can be localized to the diseased tissue to promote necessary proliferation and engraftment. Thus, the invention takes into account not only the cell type to be transplanted, but also the cell type in combination with the appropriate biomaterials and grafting method for the most efficient and successful transplant therapies. Grafting technologies of the present invention are translatable to therapeutic uses in patients and provide alternative treatments for regenerative medicine to reconstitute diseased or dysfunctional tissue. Indeed, although the present application has been largely drafted with diabetes as representative of a strategy for treatment with grafting into the hepato-pancreatic common duct, the strategy is also applicable for treatment of liver diseases by grafting into the bile duct wall in a different region of the biliary tree, one near to the liver.

Cell Sourcing

According to the invention, desired cell populations may be obtained directly from a donor having "normal," "healthy" tissue and/or cells, meaning any tissue and/or cells that is/are not afflicted with disease or dysfunction. Of course, such a cell population may be obtained from a person suffering from an organ with disease or dysfunction, albeit from a portion of the organ that is not in such a condition. The cells may be sourced from any appropriate mammalian tissue, regardless of age, including fetal, neonatal, pediatric, and adult tissue, preferably gallbladder or biliary tissue connected to intact livers and pancreases.

Multipotent human biliary tree stem cells (hBTSCs) are the preferred cells for this inventive method and can be isolated from the gallbladder or any portion of the biliary tree tissue but are found at especially high numbers in the peribiliary glands and at the branching points of the tree, particularly in the hepato-pancreatic common duct or in the large intrahepatic bile ducts. In the interest of clarity for this application, the term "Biliary Tree Stem Cell" will be used herein to refer to the inventive mammalian multipotent stem or progenitor cell, cell populations comprising such inventive cells, and cells populations enriched for the inventive cells. See U.S. patent application Ser. No. 12/926,161, the disclosure of which is incorporated herein in its entirety by reference in this respect.

Human gallbladders do not have peribiliary glands; however, they contain a population of stem/progenitor cells within mucosal crypts and with overlapping features of hBTSCs. Therefore, the term "Biliary Tree Stem Cells" includes also stem/progenitor cells isolable from human gallbladders. This is an advantage given that removal of the gallbladder is done routinely for many reasons and with minimal negative consequences to the patient and allows for autologous cell therapies or allogeneic ones depending on the need of the patient being treated with cell therapy.

Biliary tree stem cells can be differentiated into multiple endodermal fates. Indeed, the stem cells may be induced to differentiate into mature cell types of several endodermal lineages including pancreas or liver. For pancreatic islet cells, the biliary tree stem cells are incubated with a medium that is modified from Kubota's Medium prepared without glucocorticoids and then by supplementation with copper ($10^{-12}$M), calcium (levels approx. 0.6 mM), 10 ng/ml basic fibroblast growth factor (bFGF), 2% B27, 0.1 mM ascorbic acid, 0.25 µM cyclopamine, and 0.5 µM RA (retinoic acid). After 4-5 days, the bFGF is replaced with 50 ng/ml exendin-4. The matrix scaffolds for the grafts used are comprised of 60% type IV collagen and laminin (these two at 1:1 ratio) and 40% hyaluronans, and are also effective with the addition of type VI collagen and nidogen to the mix of matrix components. One can also use simple hyaluronans plus the hormonal mix with the understanding that the lineage restriction process will go more slowly than occurs with hyaluronans plus other matrix components.

Cells may also be sourced for different therapies from "lineage-staged" populations based on the therapeutic need. For example, later-stage "mature" cells may be preferred in cases where there is a need for rapid acquisition of functions offered only by the late lineage cells, or if the recipient has a lineage-dependent virus that preferentially infects the stem cells and/or progenitors such as occurs with hepatitis C or papilloma virus. In any event, "progenitor" cells may be used to establish any of the lineage stages of their respective tissue(s). For a discussion of lineage-staged liver cell populations and method of their isolation, see U.S. patent application Ser. Nos. 11/560,049 and 12/213,100, the disclosures of which are both incorporated in their entirety herein by reference.

Samples of biliary tree tissue can be dissected surgically from livers or pancreas obtained for and then rejected for transplant due to reasons such as steatosis; anatomical abnormality, or major vascular disease; or they can be obtained from resection material. They can be from gallbladders removed for various reasons. The tissue is then divided into segments and processed further. Segments that are especially rich in the biliary tree stem cells include: the large intrahepatic bile ducts, the hilum, common hepatic duct, cystic duct, common duct, common hepato-pancreatic duct and gallbladder. Each part can be further dissected into pieces cutting along the longitudinal diameter.

The biliary tree stem cells have been shown to give rise to multiple endodermal fates including liver, biliary tree, and pancreas cells. As primitive stem cells, they express pluripotency genes (Nanog, SOX2, KLF4, OCT4, SALL4); hepatic and pancreatic endodermal transcription factors (e.g., SOX17, SOX 9, FOXA2, PDX 1;) and surface markers typical for stem cells including LGR5 (leucine-rich repeat-containing G protein coupled receptor 5), CD44 (hyaluronan receptor), CD133 (prominin); CD56/Neuronal cell adhesion molecule or NCAM); and CXCR4 (CXC-chemokine receptor 4). As they begin to mature towards a pancreatic or hepatic fate, they acquire expression of CD326/Epithelial cell adhesion molecule or EpCAM.

Furthermore, with progression in the maturational lineage towards liver, the biliary tree stem cells lose pancreatic markers (e.g., PDX1) and acquire and then steadily increase expression of early lineage markers of the liver such as HNF6, HES1, alpha-fetoprotein (AFP) and albumin).

With maturational progression towards pancreas, the biliary tree stem cells lose hepatic markers (e.g., SOX 17) but not pancreatic ones (e.g., PDX1) and acquire and then steadily increase expression of early lineage markers of the pancreas (e.g., NGN3, MUC6, insulin, amylase). Notably, PDX1 and NGN3 are known to be essential for development of the pancreas and the endocrine pancreas, respectively.

However, the biliary tree stem cells do not express (or only faintly express) markers of mature cells such as the mature markers of cholangiocytes (e.g., secretin receptor, CFTR, aquaporins), hepatocytes (e.g., tyrosine aminotransferase or TAT, transferrin, or "late" P450s such as P450-3A4) or islet cells (e.g., glucagon, somatostatin, high levels of insulin). They do not express at all markers for mesenchymal cells (e.g., CD146, desmin), endothelial cells (e.g., VEGF receptor, CD31, Van Willebrand Factor) or hemopoietic cells (e.g., CD45). The pattern of expression of the antigens is stable throughout the life of the cultures as long as they are maintained under self-replication conditions consisting of Kubota's Medium or its equivalent and with a substratum of culture plastic or hyaluronans.

These phenotypic traits can be determined using endpoint and quantitative (q)-RT-PCR assays and by immunohistochemistry of tissue in vivo, of freshly isolated cells, or of cultured cells. The co-expression in the same cells or in cells within the same peribiliary gland of multiple markers of endodermal stem/progenitors (e.g., SOX 9, SOX17, PDX1, NGN3, FOXA2) is a unique and surprising feature that is distinctive from the findings with respect to embryonic stem (ES) cells undergoing lineage restriction to pancreas and in which these transcription factors are observed sequentially, but not all at the same time. Furthermore, the expression of these transcription factors is absent in mature biliary cells at the lumenal surface of the bile ducts.

The biliary tree stem cells of the present invention, as explained above, are stem/progenitors giving rise to mature cells of the multiple endodermal tissues including liver, biliary tree, and pancreas.

The stem cell populations from human biliary tree tissue can be isolated by immunoselection technologies (e.g., flow cytometry, panning, magnetic bead isolation). Alternatively, or in addition to immunoselection, the biliary tree stem cells may be identified and isolated by culture selection technologies that comprise tissue culturing the cells under specific conditions. For example, cell suspensions prepared from the biliary tree tissue may be plated onto plastic or onto (or embedded in) hyaluronans. In other embodiments, the plastic is coated optionally with matrix components found in embryonic/fetal tissues such as type III collagen or hyaluronans, or combinations thereof.

The medium used for culture selection, serum-free Kubota's Medium or its equivalent, is strongly selective for the survival and proliferation of the biliary tree stem cells and their partner mesenchymal cells, angioblasts and stellate cell precursors, but is not selective for mature cells of the biliary tree. The essence of this medium is that it is any basal medium containing no copper, low calcium (<0.5 mM), insulin, transferrin/Fe, free fatty acids bound to purified albumin and, optionally, also high density lipoprotein.

Kubota's Medium or its equivalent is serum-free and contains only purified and a defined mix of hormones, growth factors, and nutrients. More specifically, the medium is comprised of a serum-free basal medium (e.g., RPMI 1640 or DME/F12) containing no copper, low calcium (<0.5 mM) and supplemented with insulin (5 μg/ml), transferrin/Fe (5 μg/ml), high density lipoprotein (10 μg/ml), selenium ($10^{-10}$ M), zinc ($10^{-12}$ M), nicotinamide (5 μg/ml), and a mixture of purified free fatty acids bound to a form of purified albumin. The detailed methods for the preparation of this media have been published elsewhere, e.g., Kubota H, Reid L M, Proceedings of the National Academy of Sciences (USA) 2000; 97:12132-12137, the disclosure of which is incorporated herein in its entirety by reference.

In addition to the cells required to provide the "function" per se of a diseased or dysfunctional internal organ, the graft preferably includes additional cellular components that preferably mimic the categories of cells comprising the epithelial-mesenchymal cell relationship, the cellular foundation of all tissues. Epithelial-mesenchymal cell relationships are distinct at every maturational lineage stage. Epithelial stem cells are partnered with mesenchymal stem cells and their maturation is coordinate with each other as they mature to all the various adult cell types within a tissue. The interactions between the two are mediated by paracrine signals that comprise soluble signals (e.g., growth factors) and extracellular matrix components.

According to one embodiment of the invention, the isolated cell populations are combined with known paracrine signals (discussed below) and "native" epithelial-mesenchymal partners, as needed, to optimize the graft. Thus, the grafts will comprise the epithelial stem cells (e.g. the hepatic stem cells) mixed together with their native mesenchymal partners (e.g. angioblasts). For a transit amplifying cell niche graft, hepatoblasts can be partnered with precursors to hepatic stellate cells and/or endothelia. In some grafts one can make a mix of the two sets of epithelial-mesenchymal partners: hepatic stem cells with angioblasts and hepatoblasts with hepatic stellate cell precursors and endothelial cell precursors to optimize the establishment of the liver cells in the host tissue. The microenvironment of the graft into which the cells are seeded will be comprised of the paracrine signals, matrix and soluble signals, that are produced at the relevant lineage stages used for the graft.

Grafts can also be tailored to manage a disease state. For example, to minimize effects of lineage dependent viruses (e.g., certain hepatitis viruses) that infect early lineage stages and then mature coordinately with the host cells, one can prepare grafts of later lineage stage (e.g., hepatocytes and their native partners, sinusoidal endothelial cells) that are non-permissive for viral infection by some viruses.

An example of a stem cell graft, using pancreatic cell therapies as a model, would comprise the biliary tree stem cells and angioblasts. In contrast, a graft of "mature" liver cells would comprise hepatocytes, mature endothelial cells and mature stellate cells. For a discussion of the epithelial-mesenchymal cell relationship of livers, see U.S. patent application Ser. No. 11/753,326, the disclosure of which is incorporated in its entirety herein by reference.

Grafting Materials

The use of biomaterials according to the invention provides a scaffold for cell support and signals that assist in the success of the grafting and regenerative processes. As tissue of solid organs in an organism undergo constant remodeling, dissociated cells tend to reform their native structures under appropriate environmental conditions. For a discussion on grafting methods suitable for application with the present invention, see U.S. patent application Ser. No. 13/102,939, the disclosure of which are both incorporated in their entirety herein by reference.

In all tissues, the paracrine signaling comprises both soluble (myriad growth factors and hormones) and insoluble (extracellular matrix (ECM) signals. Synergistic effects between the soluble and (insoluble) matrix factors dictate growth and differentiative responses by the transplanted cells. The matrix components are the primary determinants of attachment, survival, cell shape (as well as the organization of the cytoskeleton), and stabilization of requisite cell surface receptors that prime the cells for responses to specific extracellular signals.

The ECM is known to regulate cell morphology, growth and cellular gene expression. Tissue-specific chemistries similar to that in vivo may be achieved ex vivo by using purified ECM components. Many of these are available commercially and are conducive to cell behavior mimicking that in vivo.

Suitable matrix components include collagens, adhesion molecules (e.g., cell adhesion molecules, tight junctions, basal adhesion molecules), elastins, and carbohydrates that form proteoglycans (PGs) and glycosaminoglycans (GAGs). Each of these categories defines a genus of molecules. For example, there are at least 25 collagen types present, each one encoded by distinct genes and with unique regulation and functions. The various matrix components that are proteins (e.g., collagens, attachment proteins) are generally available commercially. Tissue-specific forms of glycosaminoglycans (e.g., tissue-specific heparins) can be purified from natural sources and/or a few can be synthesized. To be sure, the grafts can be successful without the glycosaminoglycans, but may take longer and may not have some of the specificities that the glycosaminoglycans dictate.

Additional biomaterials that might offer methods of grafting include inorganic, natural materials like chitosan and alginate as well as many synthetic, biodegradable and biocompatible polymers. These materials are often "solidified" (e.g., made into a gel) through methods including thermal gelation, photo cross-linking, or chemical cross-linking. With each method, however, it is necessary to account for cell damage (e.g., from excessive temperature ranges, UV exposure). For a more detailed discussion of biomaterials, specifically the use of hyaluronan hydrogels, see U.S. patent application Ser. No. 12/073,420, the disclosure of which is incorporated in its entirety herein by reference.

The particular selection of which matrix components may be guided by gradients in vivo, for example, that change from the stem cell compartment to the late lineage stage cells. The graft biomaterials preferably mimic the matrix chemistry of the particular lineage stages desired for the graft. The efficacy of the chosen mix of matrix components may be assayed in ex vivo studies using purified matrix components and soluble signals, many of which are available commercially, according to good manufacturing practice (GMP) protocol. The biomaterials selected for the graft preferably elicit the appropriate growth and differentiation responses required by the cells for a successful transplantation.

Concerning the liver, the matrix chemistry associated with the hepatic stem cells is present in the peribiliary glands of the large intrahepatic bile ducts and in the ductal plates (fetal and neonatal livers) that transition to become the canals of Hering (pediatric and adult livers). The later lineage stages of hepatic parenchymal cells are in the Space of Disse, the area located between the parenchyma and the endothelia or other forms of mesenchymal cells.

In addition to a change in cell maturity within the different zones of the liver, a change in matrix chemistries is also observed. The matrix chemistry in the ductal plates or canals of Hering (and potentially the intrahepatic peribiliary glands) is similar to that found in fetal livers and consists of type III and V collagens (no type I collagen), hyaluronans, forms of laminin that bind to alpha6/beta4 integrin (e.g., laminin 5), and forms of chondroitin sulfate proteoglycans (CS-PGs) that have minimal sulfation.

This zone transitions to a different matrix chemistry in the region adjacent to the canals of Hering and associated with hepatoblasts and consists of type IV, V and VI collagens, hyaluronans, forms of laminin that bind to alpha/beta1 integrin, more sulfated CS-PGS and weakly sulfated heparan sulfate proteoglycans (HS-PGs).

The transit amplifying cell compartment transitions to yet later lineage stages, and with each successive stage, the matrix chemistry becomes more stable (e.g., more highly stable collagens), turns over less, and contains more highly sulfated forms of GAGs and PGs. The most mature cells are associated with forms of heparin-PGs (HP-PGs), meaning that myriad proteins (e.g., growth factors and hormones, coagulation proteins) can bind to the matrix and be held stably there via binding to the discrete and specific sulfation patterns in the GAGs. Thus, the matrix chemistry transitions from its start point in the stem cell niche having labile matrix chemistry associated with high turnover and minimal sulfation (and therefore minimal binding of signals in a stable fashion near to the cells) to stable matrix chemistries with increasing amounts of sulfation (and therefore higher and higher levels of signal binding held near to the cells).

Concerning the pancreas, the transitions in matrix chemistry from stem cells to mature cells give rise to distinct chemical compositions associated with the acinar cells versus the islets. Among the distinctions known are that islets are especially rich in forms of heparan sulfate proteoglycans (glypicans and syndecans), in nidogen, and in network collagens (e.g. type IV, VI), whereas the acinar cells are rich in forms of chondroitin sulfate proteoglycans, fibronectins, and various fibrillar collagens. As well, the matrix chemistry associated with pancreatic stem/progenitor cells is present in the peribiliary glands of the hepato-pancreatic duct. Matrices associated with later lineage stages of pancreatic parenchymal cells are in pancreatic ducts and pancreatic duct glands. Matrices of mature stages include those in contact with pancreatic acinar tissue and pancreatic islet cells.

Hence, the present invention takes into consideration that the chemistry of the matrix molecules changes with maturational stages, with host age, and with disease states. Grafting with the appropriate materials should optimize engraftment of transplanted cells in a tissue, prevent dispersal of the cells to ectopic sites, minimize embolization problems, and enhance the ability of the cells to integrate within the tissue as rapidly as possible. Moreover, the factors within the graft can also be chosen to minimize immunogenicity problems.

In the case of human livers or of human biliary tree tissue, cells may be cultured under serum free conditions. Human hepatic stem cell or hepatoblasts (hHpSC or hHB) can be grafted by themselves, or in combination with angioblasts/endothelial cells. Cells can be suspended in thiolated and chemically-modified HA (CMHA-S, or Glycosil, Glycosan BioSystems, Salt Lake City, Utah) and in KM (Kubota's Medium) and loaded into one of the syringes of a set of paired syringes. The other syringe may be loaded with a cross-linker, e.g., poly(ethylene glycol) diacrylate or PEGDA, prepared in KM. The two syringes are coupled by a needle that flares into two luer lock connections. Thus, the cells in hydrogel and the cross-linker can emerge through one needle to allow for rapid cross-linking of the CMHA-S into a gel upon injection.

The cell suspension in CMHA-S and crosslinker can be either directly injected or grafted to the target tissue using a pouch made from tissue (e.g., omentum tissue) or from a synthetic material (e.g., spider silk). Alternatively, the cells may be encapsulated in Glycosil without the use of a PEGDA crosslinker by allowing the suspension to stand overnight in air, leading to disulfide bond crosslinking to a soft, viscous hydrogel. In addition, other thiol-modified macromonomers, e.g., gelatin-DTPH, heparin-DTPH, chondroitin sulfate-DTPH, may be added to give a covalent network mimicking the matrix chemistry of particular niches in vivo. In another manifestation, polypeptides containing cysteine or thiol residues can be coupled to the PEGDA prior to adding the PEGDA to the Glycosil, allowing specific polypeptide signals to be incorporated into the hydrogel. Alternatively, any polypeptide, growth factor or matrix component such as an isoform of a collagen, laminin, vitronectin, fibronectin, etc., may be added to the Glycosil and cell solution prior to crosslinking, allowing passive capture of important polypeptide components in the hydrogel.

Hyaluronans: Hyaluronans (HAs) are members of one of the 6 large glycosaminoglycan (GAG) families of carbohydrates, all being polymers of a uronic acid and an aminosugar [1-3]. The other families comprise the chondroitin sulfates (CS, [glucuronic acid-galactosamine]$_x$), dermatan sulfates (DS, more highly sulfated [glucuronic acid-galactosamine]$_x$), heparan sulfates (HS, [glucuronic acid-glucosamine]$_x$), heparins (HP, more highly sulfated [gluronic acid-glucosamine]$_x$) and keratan sulfates (KS, [galactose-N-acetylglucosamine]$_x$).

HAs are composed of a disaccharide unit of glucosamine and gluronic acid linked by β1-4, β1-3 bonds. Biologically, the polymeric glycan is composed of linear repeats of a few hundreds to as many as 20,000 or more of disaccharide units. The HAs have molecular masses typically ranging from 100,000 Da in serum to as much as 2,000,000 in synovial fluid, to as much as 8,000,000 in umbilical cords and the vitreous. Because of its high negative charge density, HA attracts positive ions, drawing in water. This hydration allows HA to support very compressive loads. HAs are located in all tissues and body fluids, and most abundant in soft connective tissue, and the natural water carrying capacity lends itself to speculation to other roles including influences of tissue form and function. It is found in extracellular matrix, on the cell surface and inside the cell.

Native forms of HA chemistry are diverse. The most common variable is the chain length. Some are high molecular weight due to having long carbohydrate chains (e.g., those in the coxcomb of gallinaceous birds and in umbilical cords) and others are low molecular weight due to having short chains (e.g., from bacterial cultures). The chain length of HAs plays a key role in the biological functions elicited. A low molecular weight HA (below $3.5 \times 10^4$ kDa) may induce the cytokine activity that is associated with matrix turnover and is shown to be related to inflammation in tissues. A high molecular weight (above $2 \times 10^5$ kDa) may inhibit cell proliferation. Small HA fragments, between 1-4 kDa, have been shown to increase angiogenesis.

Native forms of HA have been modified to introduce desired properties (e.g., modification of the HAs to have thiol groups allowing the thiol to be used for binding of other matrix components or hormones or for novel forms of cross-linking). Also, there are forms of cross-linking that occur in nature (e.g., regulated by oxygen) and yet others that have been introduced artificially by treatment of native and modified HAs with certain reagents (e.g., akylating agents) or, as noted above, establishment of modified HAs that make them permissive to unique forms of cross-linking (e.g., disulfide bridge formation in the thiol-modified HAs).

According to the invention, thiol-modified HAs and in situ polymerizable techniques used for them are some of the forms that are preferred. These techniques involve disulfide crosslinking of thiolated carboxymethylated HA, known as CMHA-S or Glycosil. For in vivo studies, HA with lower molecular weight, e.g., 70-250 kDa, can be used, since the crosslinking, either disulfide or PEGDA, creates a hydrogel of very high molecular size. A thiol-reactive linker, polyethylene glycol diacrylate (PEGDA) crosslinker, is suitable for both cell encapsulation and in vivo injections. This combined Glycosil-PEGDA material crosslinks through a covalent reaction and in a matter of minutes, is biocompatible and allows for cell growth and profileration.

The hydrogel material, Glycosil, takes into account the gel properties conducive to tissue engineering of stem cells in vivo. Glycosil is part of the semi-synthetic extracellular matrix (sECM) technology available from Glycosan Biosciences in Salt Lake City, Utah (now a subdivision of Biotime in Alameda, Calif.). A variety of products in the Extracel and HyStem trademarked lines are commercially available. These materials are biocompatible, biodegradable, and non-immunogenic.

Furthermore, Glycosil and Extralink can be easily combined with other ECM materials for tissue engineering applications. HA can be obtained from many commercial sources, with a preference for bacterial fermentation using either Streptomyces strains (e.g., Genzyme, LifeCore, Nova-Matrix, and others) or bacterial-fermentation process using Bacillus subtilis as the host in an ISO 9001:2000 process (unique to Novozymes).

The ideal ratios of the cell populations should replicate those found in vivo and in cell suspensions of the tissue. A mix of cells allows for maturation of progenitor cells and/or maintenance of the adult cell types concomitant with the development of requisite vascularization. In this way, a composite microenvironment using hyaluronans as a base for a complex containing multiple matrix components and soluble factors and designed to mimic specific micro-environmental niches comprised of specific sets of paracrine signals produced by an epithelial cell and a mesenchymal cell at a specific maturational lineage stage is achieved. See U.S. patent application No. 61/332,441, the disclosure of which is incorporated herein in its entirety by reference.

The microenvironment of a stem cell niche in the liver consists of the paracrine signals between the hepatic stem cell and angioblasts. It is comprised of hyaluronans, type III collagen, specific forms of laminin (e.g., laminin 5), a unique form of chondroitin sulfate proteoglycan (CS-PG) that has almost no sulfation and a soluble signal/medium composition close to or exactly that of "Kubota's Medium", a medium developed for hepatic stem/progenitors. No other factors are strictly required, though effects can be observed by supplementation with stem cell factor, R-spondin, leukemia inhibitory factor (LIF), and/or certain interleukins (e.g., IL 6, IL11 and TGF-β1). The stem cell niche form of CS-PG is not yet available The transit amplifying cell microenvironment in the liver is morphologically between that of the hepatoblasts and hepatic stellate cell precursors or endothelial cell precursors. The components of this microenvironment include hyaluronans, type IV collagen, specific forms of laminins that bind to αβ1 integrins, more sulfated CS-PGs, forms of heparan sulfate-proteoglycans (HS-PGs), and soluble signals that include epidermal growth factor (EGF), hepatocyte growth factor (HGF), stromal cell-derived growth factor (SGF), and retinoids (e.g., vitamin A).

Transplantation Methods

Injectable grafts have an advantage in that they can fill any deficit shape or space (e.g., damaged organs or tissues).

According to this method, cells are co-cultured and delivered in a cell suspension embedded in gelable biomaterials, which solidify in situ using various crosslinking methods. The suspension may be directly delivered to the walls of the hepato-pancreatic common duct either by endoscopy or by laparoscopy or as a patch in cuff-shape around the duct and containing the hydrogel placed against the outside wall of the duct. They can be immobilized in the wall by providing a cross-linker, PEGDA, that will cause the hyaluronan-matrix mixture to gel. The procedure should be able to be done reasonably rapidly and with minimal morbidity to patients.

Direct Injection into the Bile Duct Wall. The fibromuscular walls of the hepato-pancreatic common duct are composed of layers of muscular and connective tissues that adhere to and envelope the epithelial structures of the hepato-pancreatic common duct. These layers of fibromuscular tissue form a sleeve that extends from the opening of the ampulla of Vater to the separation of the common bile duct and the duct of Wirsung. Separate structures of fibromuscular tissues continue along these two structures. Fibromuscular walls are embedded in the parenchymal tissue of the head of the pancreas, or in fibro-adipose tissue, depending on anatomical variations and age of the individual.

Patch graft onto the surface of the Bile Duct Wall. Alternatively, the graft of the stem/progenitor cells admixed within appropriate biomaterials and with relevant soluble signals can be placed within a covering (e.g. spider silk, omentum) that is surgically glued to the bile duct or around the bile duct (that is as a cuff encircling the duct). The graft of stem cells will interact with the extramural peribiliary glands tethered to the surface of bile ducts. Thus, the grafted stem/progenitors can be being incorporated into the duct through the outside of the duct.

Both laparoscopic surgery or endocoscopic delivery can utilize an intraluminal approach. Briefly, an endoscope could be inserted through the mouth and threaded through the stomach to the duodenum. Using a sideport on the endoscope, one can enter into the hepato-pancreatic common duct through the ampulla. The hepato-pancreatic common duct would be used for the site of delivery of cells intended for the pancreas. The endoscope could be moved along the bile duct to reach a site near the liver for delivery of cells targeting the liver. Using this approach, one can transplant the cells as a graft into the periductal region; the grafting strategy should facilitate the engraftment of the cells. The procedure would have to be performed under general sedation.

In laparoscopic surgery, a patient undergoes general anesthesia and small incisions (typically less than 1 cm) are made in the skin and fascia to allow placement of laparoscopic ports and instruments. A camera is introduced into the peritoneal cavity to allow visual guidance and other instruments including an ultrasound can also be introduced into the abdomen. These visual techniques provide a means to identify the pancreas and its parenchymal features including the pancreatic duct. Through ultrasound or other imaging guidance, a surgeon directs a small gauge needle into the preferred location of the pancreas for delivery of the cells. This approach allows the surgeon to identify and control bleeding, minimize inadvertent delivery or injury to surrounding organs and to provide a mechanism to minimize morbidity associated with the intervention.

Injection may also be performed, for example, using a double barreled syringe as described hereinabove. Briefly, the cell-matrix-medium mixture is loaded into one side of the syringe with connecting needle to the other syringe containing the cross-linker PEGDA. The mixture can be injected through a 25 gauge needle directly into hepato-pancreatic common duct and instantly cross-linked to form a hydrogel. The use of CMHA-S with PEGDA at pH 7.4 allows cell encapsulation as well as injection in vivo, since the crosslinking reaction occurs over a 1-2 min time frame.

Inorganic, natural materials like chitosan, alginate, hylauronic acid, fibrin, gelatin, as well as many synthetic polymers can suffice as biomaterials for injections. These materials are often solidified through methods including thermal gelation, photo cross-linking, or chemical cross-linking. The cell suspension may also be supplemented with soluble signals or specific matrix components. Since these grafts can be relatively easily injected into a target area, there is no (or minimal) need for invasive surgery, which reduces cost, patient discomfort, risk of infection, and scar formation. CMHA may also be used for injectable material for tissue engineering due to its long-lasting effect while maintaining biocompatibility. Cross-linking methods also maintain the material biocompatibility, and its presence in extensive areas of regenerative or stem/progenitor niches make it an attractive injectable material.

In some embodiments, a graft may be designed for placement directly onto a surface of the walls of the hepato-pancreatic common duct, in which case the graft would be held in place with a biocompatible and biodegradable covering ("band aid"). The cells so delivered should give rise to descendants that can migrate into the pancreas to correct the diseased or genetic condition. If there is difficulty for the migration to occur through the bile duct surface, then the surface can be abraded chemically or surgically to allow access.

Unless otherwise defined, all technical and scientific terms used herein have the same meaning as commonly understood by one of ordinary skill in the art to which this invention belongs. All publications, patent applications, patents, and other references mentioned herein are incorporated by reference in their entirety. In case of conflict, the present specification, including definitions, will control. In addition, the materials, methods, and examples are illustrative only and not intended to be limiting.

The invention now will be described in particularity with the following illustrative examples; however, the scope of the present invention is not intended to be, and shall not be, limited to the exemplified embodiments below.

EXAMPLE 1

Example of Efficacy of Grafting Strategy using Hyaluronan Grafts

Mouse hepatic progenitor cells were isolated from a host C57/BL6 mouse (4-5 weeks) according to reported protocols. For the "grafting" studies, a GFP reporter was introduced into the hepatic progenitor cells. The cells were then mixed with hyaluronan (HA) hydrogels and the HA cross-linked prior to introduction into a subject mouse. For introduction/transplantation, mice were anesthetized with ketamine (90-120 mg/kg) and xylazine (10 mg/kg), and their abdomens were opened. The cells, with or without HA, were then slowly injected into the liver. The incision site was closed and animals were given 0.1 mg/kg buprenorphine every 12 hrs for 48 hrs. After 48 hrs, animals were euthanized, and tissue was removed, fixed, and sectioned for histology.

To determine cell localization within the murine models, "control" hepatic progenitor cells were infected for 4 hrs at 37° C. with a luciferase-expressing adenoviral vector at 50 POI. Survival surgery was performed as described above, and cells (1-1.5E6) were injected into the liver lobe by a vascular route (hepatic artery or portal vein) or into the hepato-pancreatic common duct by direct injection or by grafting. Just prior to imaging, mice were injected subcutaneously with luciferin, producing a luminescent signal by the transplanted cells. Using an IVIS Kinetic optical imager, the localization of cells within the mice was determined Experimental hosts were injected with cells suspended in buffer with HA.

At 24 hrs, "control" cells injected without HA grafting were found both in the liver and lung. At 72 hrs, however, most cells could not be located with only a few identifiable cells remaining in the liver. The grafted cells according to the invention, by contrast, were observed as a group of cells successfully integrated into the liver at both 24 and 72 hrs, and remained present even after two weeks. Cells transplanted via this stem cell niche graft were also seen to localize almost exclusively to liver tissue and were not found in other tissues by assays on randomized histological samples.

EXAMPLE 2

Pancreatic Stem Cells

Wang, et al., *Stem Cells*. 2013; 31(9):1966-1979, incorporated herein it its entirety by reference. Proximal (PBGs)-to-distal (PDGs) maturational lineages start near the duodenum with cells expressing markers of pluripotency (NANOG, OCT4, SOX2), proliferation (Ki67), self-replication (SALL4), and early hepato-pancreatic commitment (SOX9, SOX17, PDX1, LGR5), transitioning to PDG cells with no expression of pluripotency or self-replication markers, maintenance of pancreatic genes (PDX1), and expression of markers of pancreatic endocrine maturation (NGN3, MUC6, insulin). Radial-axis lineages start in PBGs near the ducts' fibromuscular layers with stem cells and end at the ducts' lumens with cells devoid of stem cell traits and positive for pancreatic endocrine genes.

Biliary tree-derived cells behave as stem cells in culture under expansion conditions, culture plastic and serum-free Kubota's Medium, proliferating for months as undifferentiated cells, whereas pancreas-derived cells underwent only ~8-10 divisions, then partially differentiated towards an islet fate. Biliary tree-derived cells proved precursors of pancreas' committed progenitors. Both could be driven by 3-dimensional conditions, islet-derived matrix components and a serum-free, hormonally defined medium for an islet fate (HDM-P), to form spheroids with ultrastructural, electrophysiological and functional characteristics of neoislets, including glucose regulatability. Implantation of these neoislets into epididymal fat pads of immuno-compromised mice, chemically rendered diabetic, resulted in secretion of human C-peptide, regulatable by glucose, and able to alleviate hyperglycemia in hosts. The biliary tree-derived stem cells and their connections to pancreatic committed progenitors constitute a biological framework for life-long pancreatic organogenesis

EXAMPLE 3

Stem Cells in the Gallbladder

Gallbladders were obtained from organ donors and laparoscopic surgery for symptomatic cholelithiasias. Tissues or isolated cells were characterized by immunohistochemistry and flow cytometry. EpCAM+(Epithelial Cell Adhesion Molecule) cells were immunoselected by magnetic microbeads and plated onto plastic in self-replication conditions and subsequently transferred to distinct serum-free, hormonally defined media tailored for differentiation to specific adult fates. In vivo studies were conducted in an experimental model of liver cirrhosis.

Results: the gallbladder does not have peribiliary glands, but it has stem/progenitors organized instead in mucosal crypts. These can be isolated by immune-selection for EpCAM. Approximately 10% of EpCAM+cells in situ and of immunoselected EpCAM+cells co-expressed multiple pluripotency genes and various stem cell markers; other EpCAM+cells qualified as progenitors. Single EpCAM+ cells demonstrated clonogenic expansion ex vivo with maintenance of stemness in self-replication conditions. Freshly isolated or cultured EpCAM+cells could be differentiated to multiple, distinct adult fates: cords of albumin-secreting hepatocytes, branching ducts of secretin receptor+cholangiocytes, or glucose-responsive, insulin/glucagon-secreting neoislets. EpCAM+cells transplanted in vivo in immune-compromised hosts gave rise to human albumin producing hepatocytes and to human cytokeratin7+cholangiocytes occurring in higher numbers when transplanted in cirrhotic mice. Thus, human gallbladders contain easily isolatable cells with phenotypic and biological properties of multipotent, endodermal stem cells.

EXAMPLE 4

Net Sum of Analyses Demonstrating Maturational Lineages In Situ

Cells in peribiliary glands at varying site within the biliary tree or in gallbladders were evaluated for expression of pluripotency genes, stem cell genes, and genes of mature liver or pancreas. The expression of these genes formed a pattern indicative of maturational lineages in a radial axis and proximal-to-distal axis. A summary of this is given in Table 2. The cells within the peribiliary glands nearest to the fibromusular layer were found to be the most primitive having high levels of expression of pluripotency genes (e.g. SALL4, OCT4, SOX2, KLF4, NANOG), of endodermal stem cell traits (e.g SOX9, SOX17, PDX1, LGR5), and with minimal (if any) expression of mature cell markers (albumin, insulin, CFTR). With progression towards the bile duct lumens, the pluripotency gene expression faded and there was gradual acquisition of markers for mature cell fates. If the cells were in PBGs near to the pancreas, the mature markers were insulin and other islet hormones or amylase and other markers of acinar cells. If the cells were in PBGs near to the liver, the mature markers were albumin, transferrin, P450 genes and other markers of hepatoacytes or CFTR, secretin receptor and other mature markers of cholangiocytes.

TABLE 2

Comparison of Markers of Stem/Progenitor Cells in Liver, Biliary Tree and Pancreas
Example demonstrating maturational lineages in situ within the biliary tree
Proximal-to-Distal Axis of the Maturational Lineages

| | LIVER | | | | | PANCREAS |
|---|---|---|---|---|---|---|
| Cells | Hepatoblasts -- adjacent to Canals of Hering | Hepatic Stem Cells -- in Canals of Hering | Biliary Tree Stem Cell Subpopulations in Peribiliary glands (PBGs) ENREF 8 ENREF 8 ENREF 8 ENREF 8 [subpopulations of these are also in gallbladders but there are found in crypts, not peribiliary glands] | | | Pancreatic committed progenitors in Pancreatic Duct Glands (PDGs) |
| Endodermal Markers | SOX 9+ | SOX 9+ SOX 17+ LGR5+ | SOX 9+, SOX 17+ LGR5+ | SOX 9+ SOX 17+ PDX1+ | 2. SOX 9+, PDX1+ LGR5+ | SOX 9+, PDX1+ |
| Epithelial markers | | | CK 8 and 18+, CK19+, E-cadherin+ | | | E-cadherin-, CK8, 18, 19+ |
| CAM | αβ1 integrin, ICAM-1, EpCAM | α6β4 integrin, NCAM, EpCAM | NCAM, EpCAM | NCAM | NCAM, EpCAM | Integrins EpCAM |
| | | | Integrins not yet studied | | | |
| Pluri-potency genes | Negative | Moderate levels of OCT4, NANOG, KLF4, SALL4 | Strong expression of OCT4A, SOX2, NANOG, KLF4, SALL4 | | | Negative |
| Other Stem Cell Markers | Weak CXCR4, CD133 | Strong CXCR4, CD133, CD117 | Strong CXCR4, CD133 | | | CXCR4, CD133, CD24 |
| Hedgehog Proteins | Weak Indian and Sonic | Strong Indian and Sonic[30] | Strong Sonic and Indian Hedgehog+ | | | Weak Sonic |
| Matrix proteins | Laminin**, type IV collagen | Laminin**, type III collagen | Not yet studied | | | Fetal islets have Collagen IV, V, VI, Nidogen, Elastin; fetal acinar cells have primarily fibrillar collagens, fibronectin |
| GAG/PGs | HS-PGs including syndecans, and CS-PGs | HA+, CD44+, Minimally sulfated CS-PGs | HA+, CD44+; Others not yet tested | | | Fetal islets have syndecans (HS-PG-1 and glypicans; fetal acinar cells have primarily CS-PGs |
| Liver traits | Albumin++, AFP+++, P450A7, Glycogen | Albumin ±, AFP- | Albumin±, AFP- | None | None | None |
| Pancreatic Traits | None | None | None | | ISL1, PROX 1, NeuroD, PAX4 NGN3, MUC6± | NGN3, MAFA, MUC6, Nkx6.1/ NKx6.2 (Nkx6) and Ptf1a, GLUT2 |
| MDR | MDRI- ABCG2+ | | MDR-1+, ABCG2++ | | | Negative |
| Mesenchymal Cell Traits | | | Negative for CD31, CD34, CD45, CD90, CD146, CD105 | | | |

**The laminin associated with the hepatic stem cells binds to alpha6/beta4 integrin (laminin-5); that associated with the hepatoblasts binds to alpha/beta1 integrin (laminin-111). The very primitive biliary tree stem cells found within bile ducts and near the fibromuscular layer do not express EpCAM or LGR5; those markers occur on cells that are intermediates in the process of becoming either hepatic or pancreatic stem cells.
PBGs = peribiliary glands;
PDGs = pancreatic duct glands;
HA = hyaluronans;
HS-PGs = heparan sulfate proteoglycans;
CS-PGS = chondroitin sulfate proteoglycans;
Syndecans = HS-PGs that have transmembrane core proteins;
Glypicans = HS-PGs linked to plasma membrane by phosphotidyl inositol (PI) linkages;
MDRI = multidrug resistance genes;
[2]these biliary tree stem cells are the most primitive and found near the fibromuscular layer within the bile ducts; they give rise in the radial axis maturational lineage to EpCAM+ cells.
[3]Pluripotency genes = OCT4, NANOG, KLF4, SOX2, SALL4. CD117 is found in canals of Hering and present on angioblasts that are tightly bound to the epithelial stem cells; it is hypothesized to be found in the peribiliary glands in association with the various stem cell subpopulations. Hepatoblasts, transit amplifying cells, giving rise to hepatocytic and biliary committed progenitors that do not express SOX17, pluripotency genes, LGR5, or other markers of stem cells.

While the invention has been described in connection with specific embodiments thereof, it will be understood that it is capable of further modifications and this application is intended to cover any variations, uses, or alterations of the invention following. In general, the principles of the invention and including such departures from the present disclosure as come within known or customary practice within the art to which the invention pertains and as may be applied to the essential features hereinbefore set forth and as follows in the scope of the appended claims.

We claim:
1. A method of treating a pancreatic dysfunction or condition, comprising:
   (a) obtaining a suspension of stem/progenitor cells; and
   (b) introducing the suspension into or onto the walls of the biliary tree in a subject having a pancreatic dysfunction or condition, such that a substantial portion of the cells takes residence in the wall of the biliary tree, wherein the cells mature into functional pancreatic cells and migrate to pancreas, thereby treating the pancreatic dysfunction or condition.

2. The method according to claim 1, in which the pancreatic progenitor cells are biliary tree stem cells or pancreatic stem cells or committed progenitors derived from the stem cells.

3. The method according to claim 1, in which the suspension is combined with one or more biomaterials to form a matrix complex.

4. The method according to claim 3, in which the one or more biomaterials comprise collagens, adhesion molecules, proteoglycans, hyaluronans, glycosaminoglycan chains, chitosan, alginate, and synthetic, biodegradable and biocompatible polymers, or combinations thereof.

5. The method according to claim 1, in which the suspension is combined with hormones, growth factors, cytokines, additional cells, or combinations thereof.

6. The method according to claim 5, in which the growth factors can include one or more of the fibroblast growth factors (FGFs), R-spondin, hepatocyte growth factor (HGF), epidermal growth factor (EGF), vascular endothelial cell growth factor (VEGF), insulin like growth factor I (IGF-1), insulin-like growth factor II (IGF-2), oncostatin-M, leukemia inhibitory factor (LIF), transferrin, insulin, glucocorticoids, growth hormones, estrogens, androgens, thyroid hormones, pituitary hormones, and combinations thereof.

7. The method according to claim 5, in which the additional cells comprise biliary tree stem cells, angioblasts, and precursors to endothelia and stellate cells or combinations thereof.

8. The method according to claim 1, in which the cells are obtained from a portion of the biliary tree of the subject that is not diseased or dysfunctional.

9. The method according to claim 1, in which the cells are obtained from the biliary tree of a non-autologous donor.

10. The method according to claim 1, in which the suspension is introduced by laparoscopic surgery or by endoscopy.

11. The method according to claim 1, in which the suspension of cells is introduced via injection, a graft complex with a biodegradable covering, or sponge.

12. A method of repairing the function of a pancreas in a subject having a pancreas in a diseased or dysfunctional condition, comprising:

(a) obtaining a suspension of the stem/progenitor cells; and
(b) introducing the suspension into or onto the walls of the hepato-pancreatic common duct of the subject, such that a substantial portion of the cells introduced take up residence in or on at least a portion of the pancreas as mature pancreatic cells in vivo.

13. The method according to claim 12, in which the pancreatic progenitor cells are biliary tree stem cells or pancreatic stem cells or committed progenitors derived from the stem cells.

14. The method according to claim 12, in which the suspension is combined with one or more biomaterials to form a matrix complex.

15. The method according to claim 14, in which the one or more biomaterials comprise collagens, adhesion molecules, proteoglycans, hyaluronans, glycosaminoglycan chains, chitosan, alginate, and synthetic, biodegradable and biocompatible polymers, or combinations thereof.

16. The method according to claim 12, in which the suspension is combined with hormones, growth factors, cytokines, additional cells, or combinations thereof.

17. The method according to claim 16, in which the growth factors can include one or more of the fibroblast growth factors (FGFs), R-spondin, hepatocyte growth factor (HGF), epidermal growth factor (EGF), vascular endothelial cell growth factor (VEGF), insulin like growth factor I (IGF-1), insulin-like growth factor II (IGF-2), oncostatin-M, leukemia inhibitory factor (LIF), transferrin, insulin, glucocorticoids, growth hormones, estrogens, androgens, thyroid hormones, pituitary hormones, and combinations thereof.

18. The method according to claim 16, in which the additional cells comprise biliary tree stem cells, angioblasts, and precursors to endothelia and stellate cells or combinations thereof.

19. The method according to claim 12, in which the cells are obtained from a portion of the biliary tree of the subject that is not diseased or dysfunctional.

20. The method according to claim 12, in which the cells are obtained from the biliary tree of a non-autologous donor.

21. The method according to claim 12, in which the suspension is introduced by laparoscopic surgery or by endoscopy.

22. The method according to claim 12, in which the suspension of cells is introduced via injection, a graft complex with a biodegradable covering, or sponge.

* * * * *